(12) United States Patent
Kato

(10) Patent No.: US 12,390,198 B2
(45) Date of Patent: Aug. 19, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Noriji Kato, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 322 days.

(21) Appl. No.: 18/332,534

(22) Filed: Jun. 9, 2023

(65) Prior Publication Data

US 2024/0000434 A1  Jan. 4, 2024

(30) Foreign Application Priority Data

Jul. 4, 2022  (JP) .................................. 2022-107801

(51) Int. Cl.
  *A61B 8/00* (2006.01)
  *A61B 8/08* (2006.01)

(52) U.S. Cl.
  CPC .............. *A61B 8/523* (2013.01); *A61B 8/085* (2013.01); *A61B 8/4254* (2013.01); *A61B 8/5223* (2013.01)

(58) Field of Classification Search
  CPC ......... A61B 8/523; A61B 8/52; A61B 8/5207; A61B 8/5215; A61B 8/0833; A61B 8/085; A61B 8/4245; A61B 8/4254
  See application file for complete search history.

(56) References Cited

U.S. PATENT DOCUMENTS

2014/0369583 A1  12/2014  Toji et al.

FOREIGN PATENT DOCUMENTS

| JP | H08-280678 A | 10/1996 |
|---|---|---|
| JP | 2002-306474 A | 10/2002 |
| JP | 2005-058551 A | 3/2005 |

(Continued)

OTHER PUBLICATIONS

The extended European search report issued by the European Patent Office on Dec. 1, 2023, which corresponds to European Patent Application No. 2313364.1-1126 and is related to U.S. Appl. No. 18/332,534.

(Continued)

*Primary Examiner* — Carolyn A Pehlke
(74) *Attorney, Agent, or Firm* — Studebaker Brackett PLLC

(57) ABSTRACT

There are provided an ultrasound diagnostic apparatus and a control method of the ultrasound diagnostic apparatus which can obtain a cross-sectional image in which a structure of a lesion part is accurately reproduced. An ultrasound diagnostic apparatus generates a cross-sectional image orthogonal to an observation plane on the basis of a video which is acquired during scanning by an ultrasound probe and in which a lesion part is imaged, and includes a pseudo orthogonal cross section generation unit that sets a cross section extraction line passing through the lesion part on one frame image among a plurality of frame images constituting the video, and generates a pseudo orthogonal cross-sectional image orthogonal to the observation plane by arranging, in time series, pixel values on the cross section extraction line in the plurality of frame images; and a pseudo orthogonal cross section deformation unit that non-rigidly deforms the pseudo orthogonal cross-sectional image in a horizontal direction to generate a normalized pseudo orthogonal cross-sectional image.

15 Claims, 11 Drawing Sheets

(56) References Cited

FOREIGN PATENT DOCUMENTS

JP          2014-042830 A     3/2014
KR    10-2022-0018658 A     2/2022

OTHER PUBLICATIONS

Arganda-Carreras I et al., "Non-rigid consistent registration of 2D image sequences", Physics in Medicine & Biology, vol. 55, No. 20, Sep. 30, 2010, pp. 6215-6242, Institute of Physics Publishing, doi: 10.1088/0031-9155/55/20/012.

ULTRASOUND DIAGNOSTIC APPARATUS AND CONTROL METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2022-107801, filed on Jul. 4, 2022. The above application is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which generate a cross-sectional image orthogonal to an observation plane.

2. Description of the Related Art

In the related art, in the medical field, an ultrasound diagnostic apparatus using an ultrasound image has been put to practical use. In general, an ultrasound diagnostic apparatus includes an ultrasound probe with a built-in transducer array, and an apparatus main body connected to the ultrasound probe, and the ultrasound diagnostic apparatus causes the ultrasound probe to transmit an ultrasound beam toward a subject, receives an ultrasound echo from the subject by the ultrasound probe, and electrically processes a reception signal thereof to generate an ultrasound image.

For example, in a case where an examination for a lesion part positioned at mammary glands or the like of a subject is performed by the ultrasound diagnostic apparatus, two cross sections orthogonal to each other are often imaged. In this way, in a case where two cross sections are imaged, a user such as a doctor usually switches the ultrasound probe to image the same lesion part in order to change the orientation of imaging, but this sometimes hinders the examination from being smoothly performed.

Therefore, for example, as disclosed in JP1996-280678A (JP-H08-280678A) and JP2002-306474A, a technique of generating a cross-sectional image orthogonal to the observation plane by arranging, in time series, pixel values on a designated line in a plurality of frame images constituting a video has been developed.

SUMMARY OF THE INVENTION

The speed of the ultrasound probe moved by the user in a case of capturing the plurality of frame images constituting the video may fluctuate for some reason. As described above, since temporal intervals between the plurality of frame images are not constant in a case where the scanning speed of the ultrasound probe is not constant, the structure of the lesion part in the cross-sectional image generated by the techniques of JP1996-280678A (JP-H08-280678A) and JP2002-306474A differs from the actual structure, and thus it is difficult for the user such as a doctor to perform an accurate diagnosis in some cases.

The present invention has been made in order to solve such a problem in the related art, and an object of the invention is to provide an ultrasound diagnostic apparatus and a control method of the ultrasound diagnostic apparatus which can obtain a cross-sectional image in which the structure of the lesion part is accurately reproduced.

The above object can be achieved by the following configuration.

[1] An ultrasound diagnostic apparatus that generates a cross-sectional image orthogonal to an observation plane on the basis of a video which is acquired during scanning by an ultrasound probe and in which a lesion part is imaged, the ultrasound diagnostic apparatus including a pseudo orthogonal cross section generation unit that sets a cross section extraction line passing through the lesion part on one frame image among a plurality of frame images constituting the video, and generates a pseudo orthogonal cross-sectional image orthogonal to the observation plane by arranging, in time series, pixel values on the cross section extraction line in the plurality of frame images; and a pseudo orthogonal cross section deformation unit that non-rigidly deforms the pseudo orthogonal cross-sectional image in a horizontal direction to generate a normalized pseudo orthogonal cross-sectional image.

[2] The ultrasound diagnostic apparatus described in [1], further including a measurement unit that detects the lesion part from the normalized pseudo orthogonal cross-sectional image, and measures a size of the lesion part.

[3] The ultrasound diagnostic apparatus described in [2], in which the pseudo orthogonal cross section generation unit sets a plurality of the cross section extraction lines extending in parallel to each other, and generates a plurality of the pseudo orthogonal cross-sectional images, the pseudo orthogonal cross section deformation unit generates a plurality of the normalized pseudo orthogonal cross-sectional images on the basis of the plurality of pseudo orthogonal cross-sectional images, and the measurement unit calculates a volume of the lesion part on the basis of the area of the lesion part measured from each of the plurality of normalized pseudo orthogonal cross-sectional images.

[4] The ultrasound diagnostic apparatus described in any one of [1] to [3], further including a malignancy grade calculation unit that calculates a malignancy grade of the lesion part on the basis of an image in which the lesion part is imaged.

[5] The ultrasound diagnostic apparatus described in [4], in which the malignancy grade calculation unit calculates a total malignancy grade obtained by integrating a first malignancy grade calculated on the basis of one of the plurality of frame images and a second malignancy grade calculated on the basis of the normalized pseudo orthogonal cross-sectional image.

[6] The ultrasound diagnostic apparatus described in any one of [1] to [5], further including:

a lesion detection unit that detects the lesion part for each of the plurality of frame images, in which the pseudo orthogonal cross section generation unit sets the cross section extraction line on the frame image with the largest lesion part, among the plurality of frame images.

[7] The ultrasound diagnostic apparatus described in any one of [1] to [6], in which the pseudo orthogonal cross section deformation unit includes a displacement amount estimation unit that estimates a displacement amount between a position of a pixel in the pseudo orthogonal cross-sectional image in a case where a scanning speed of the ultrasound probe is made constant and a position of a pixel in the actual pseudo orthogonal cross-sectional image, in each of time points at which the plurality of frame images are captured, and an image deformation unit that non-rigidly deforms the pseudo orthogonal cross-sectional image on the basis of the displacement amount.

[8] The ultrasound diagnostic apparatus described in [7], in which the ultrasound probe has a motion sensor that detects a moving speed of the ultrasound probe, and the displacement amount estimation unit estimates the displacement amount on the basis of the moving speed detected by the motion sensor.

[9] A control method of an ultrasound diagnostic apparatus that generates a cross-sectional image orthogonal to an observation plane on the basis of a video which is acquired during scanning by an ultrasound probe and in which a lesion part is imaged, the control method including:

setting a cross section extraction line passing through the lesion part on one frame image among a plurality of frame images constituting the video;

generating a pseudo orthogonal cross-sectional image orthogonal to the observation plane by arranging, in time series, pixel values on the cross section extraction line in the plurality of frame images; and non-rigidly deforming the pseudo orthogonal cross-sectional image in a horizontal direction to generate a normalized pseudo orthogonal cross-sectional image.

According to the present invention, an ultrasound diagnostic apparatus generates a cross-sectional image orthogonal to an observation plane on the basis of a video which is acquired during scanning by an ultrasound probe and in which a lesion part is imaged, and includes a pseudo orthogonal cross section generation unit that sets a cross section extraction line passing through the lesion part on one frame image among a plurality of frame images constituting the video, and generates a pseudo orthogonal cross-sectional image orthogonal to the observation plane by arranging, in time series, pixel values on the cross section extraction line in the plurality of frame images; and a pseudo orthogonal cross section deformation unit that non-rigidly deforms the pseudo orthogonal cross-sectional image in a horizontal direction to generate a normalized pseudo orthogonal cross-sectional image. Therefore, it is possible to obtain a cross-sectional image in which the structure of the lesion part is accurately reproduced.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
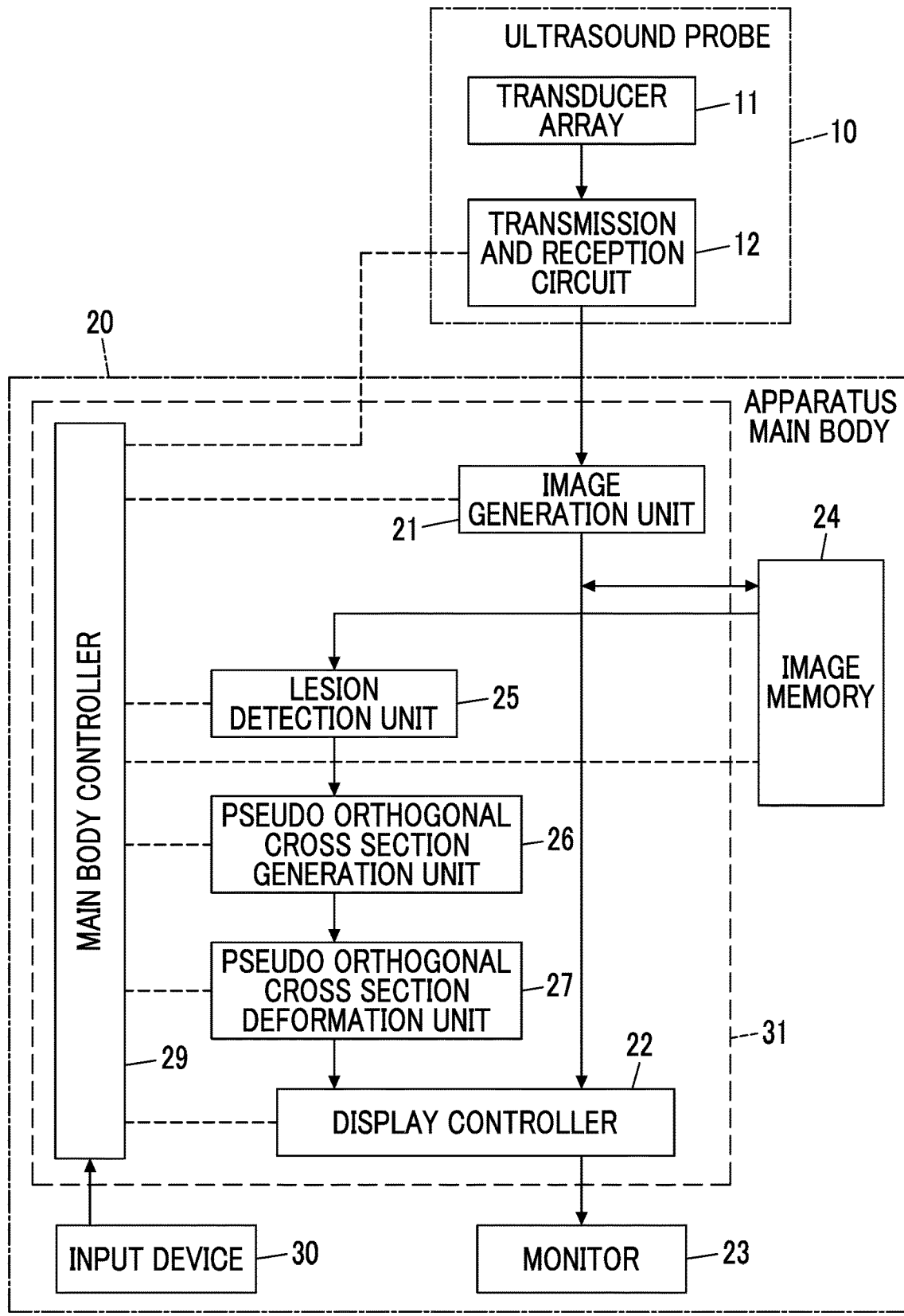
FIG. 1 is a block diagram illustrating a configuration of an ultrasound diagnostic apparatus according to a first embodiment.

FIG. 1 illustrates a configuration of an ultrasound diagnostic apparatus according to a first embodiment of the present invention. The ultrasound diagnostic apparatus includes an ultrasound probe 10 and an apparatus main body 20. The ultrasound probe 10 and the apparatus main body 20 are connected to each other in a wired manner via a cable (not illustrated).

The ultrasound probe 10 includes a transducer array 11, and a transmission and reception circuit 12 is connected to the transducer array 11.

The apparatus main body 20 has an image generation unit 21 connected to the transmission and reception circuit 12 of the ultrasound probe 10, a display controller 22 and a monitor 23 are sequentially connected to the image generation unit 21, and an image memory 24 is connected to the image generation unit 21. A lesion detection unit 25, a pseudo orthogonal cross section generation unit 26, and a pseudo orthogonal cross section deformation unit 27 are sequentially connected to the image memory 24. The pseudo orthogonal cross section deformation unit 27 is connected to the display controller 22. Further, a main body controller 29 is connected to the transmission and reception circuit 12, the image generation unit 21, the display controller 22, the image memory 24, the lesion detection unit 25, the pseudo orthogonal cross section generation unit 26, and the pseudo orthogonal cross section deformation unit 27. An input device 30 is connected to the main body controller 29.

Further, the image generation unit 21, the display controller 22, the lesion detection unit 25, the pseudo orthogonal cross section generation unit 26, the pseudo orthogonal cross section deformation unit 27, and the main body controller 29 constitute a processor 31 for the apparatus main body 20.

The transducer array 11 of the ultrasound probe 10 has a plurality of ultrasonic transducers arranged in a one-dimensional or two-dimensional manner. According to a drive signal supplied from the transmission and reception circuit 12, each of the transducers transmits an ultrasonic wave and receives a reflected wave from the subject to output an analog reception signal. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
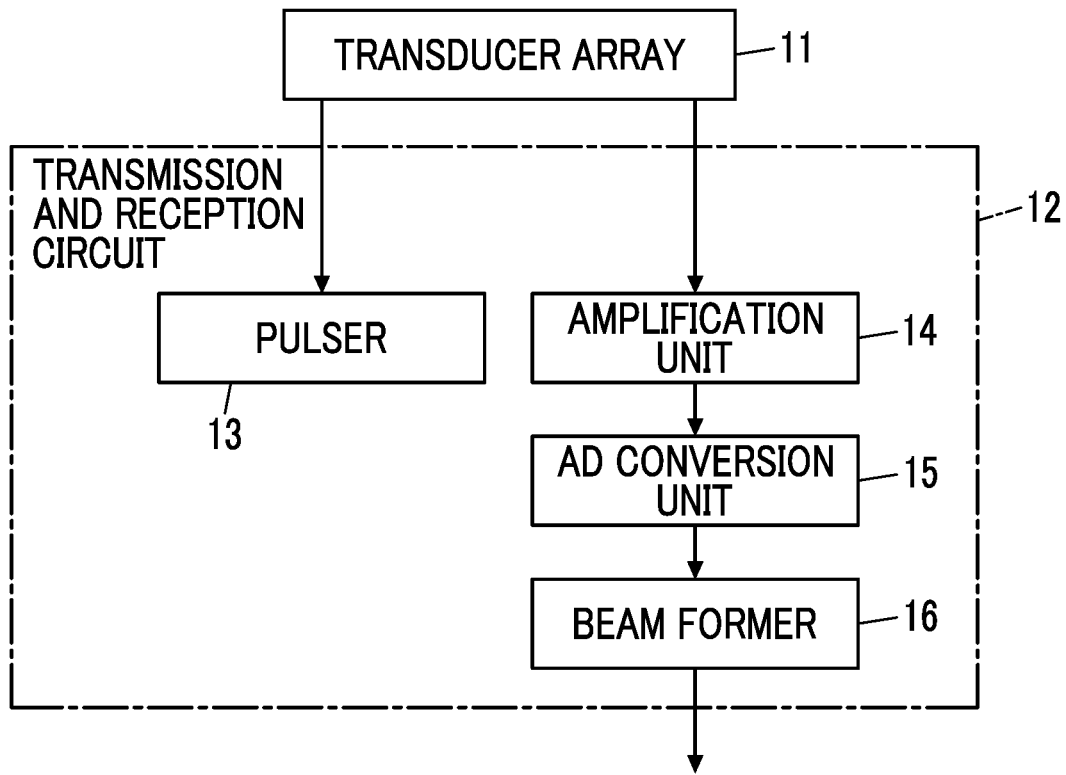
FIG. 2 is a block diagram illustrating an internal configuration of a transmission and reception circuit in the first embodiment.

The transmission and reception circuit 12 causes the transducer array 11 to transmit the ultrasonic wave and generates a sound ray signal on the basis of a reception signal acquired by the transducer array 11, under the control of the main body controller 29. As illustrated in FIG. 2, the transmission and reception circuit 12 has a pulser 13 connected to the transducer array 11, and an amplification unit 14, an analog digital (AD) conversion unit 15, and a beam former 16 that are sequentially connected in series to the transducer array 11.

The pulser 13 includes, for example, a plurality of pulse generators, and the pulser 13 adjusts the amount of delay of each drive signal so that ultrasonic waves transmitted from the plurality of transducers of the transducer array 11 form an ultrasound beam on the basis of a transmission delay pattern selected according to the control signal from the main body controller 29, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and the ultrasound echo propagates toward the transducer array 11 of the ultrasound probe 10. The ultrasound echo propagating toward the transducer array 11 in this manner is received by each transducer constituting the transducer array 11. In this case, each transducer constituting the transducer array 11 expands and contracts by receiving the propagating ultrasound echo to generate a reception signal that is an electric signal, and outputs the reception signal to the amplification unit 14.

The amplification unit 14 amplifies the signals input from each transducer constituting the transducer array 11, and transmits the amplified signals to the AD conversion unit 15. The AD conversion unit 15 converts the signal transmitted from the amplification unit 14 into digital reception data, and transmits the reception data to the beam former 16. The beam former 16 performs so-called reception focusing processing in which addition is performed by giving delays to respective pieces of the reception data converted by the AD conversion unit 15 according to a sound speed distribution or a sound speed set on the basis of a reception delay pattern selected according to the control signal from the main body controller 29. Through the reception focusing processing, a sound ray signal in which each piece of the reception data converted by the AD conversion unit 15 is phased and added and the focus of the ultrasound echo is narrowed is acquired.

Figure 3:
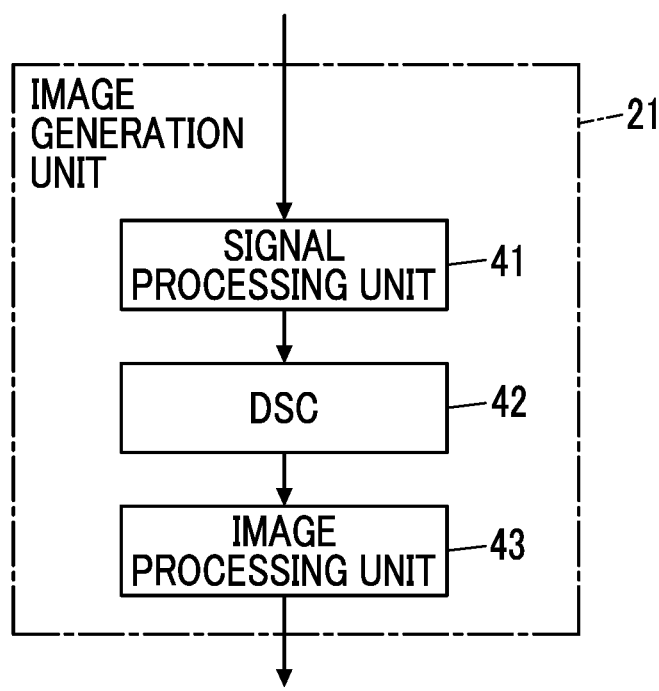
FIG. 3 is a block diagram illustrating an internal configuration of an image generation unit in the first embodiment.

As illustrated in FIG. 3, the image generation unit 21 of the apparatus main body 20 has a configuration in which a signal processing unit 41, a digital scan converter (DSC) 42, and an image processing unit 43 are sequentially connected in series.

The signal processing unit 41 generates an ultrasound image signal (B-mode image signal), which is tomographic image information regarding tissues inside the subject, by performing, on the sound ray signal sent from the transmission and reception circuit 12 of the ultrasound probe 10, correction of the attenuation due to the distance according to the depth of the reflection position of the ultrasonic wave and then performing envelope detection processing.

The DSC 42 converts (raster conversion) the ultrasound image signal generated by the signal processing unit 41 into an image signal according to a normal television signal scanning method.

The image processing unit 43 performs various kinds of necessary image processing such as gradation processing on the ultrasound image signal input from the DSC 42, and then outputs the signal representing the ultrasound image to the display controller 22 and the image memory 24. Hereinafter, the signal representing the ultrasound image generated by the image generation unit 21 in this manner is referred to as a frame image.

The image memory 24 is a memory that stores the frame image generated by the image generation unit 21 under the control of the main body controller 29. For example, the image memory 24 can store a plurality of frame images constituting a video, which are generated by consecutively imaging a region including the same lesion part of the subject by the image generation unit 21.

Here, as the image memory 24, recording media such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or the like can be used.

The lesion detection unit 25 performs an image analysis on each of the plurality of frame images stored in the image memory 24 to detect the lesion part in each of the plurality of frame images. For example, the lesion detection unit 25 can detect the lesion part using an object detection algorithm described in "REDMON, Joseph, et al. You only look once: Unified, real-time object detection. In: Proceedings of the IEEE conference on computer vision and pattern recognition. 2016. p. 779-788".

Further, the lesion detection unit 25 can detect the lesion part, for example, by a so-called template matching method of storing a plurality of template images regarding the lesion part, and using these template images. The lesion detection unit 25 can detect the lesion part by using, for example, a machine learning method described in Csurka et al.: Visual Categorization with Bags of Keypoints, Proc. of ECCV Workshop on Statistical Learning in Computer Vision, pp. 59-74 (2004), or a general image recognition method using deep learning described in Krizhevsk et al.: ImageNet Classification with Deep Convolutional Neural Networks, Advances in Neural Information Processing Systems 25, pp. 1106-1114 (2012).

Figure 4:
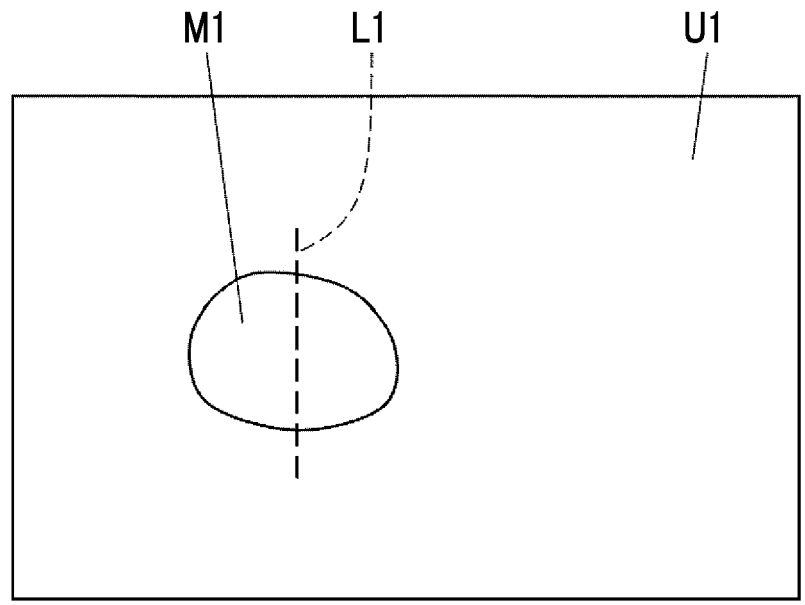
FIG. 4 is a diagram schematically illustrating a cross section extraction line.
Figure 5:
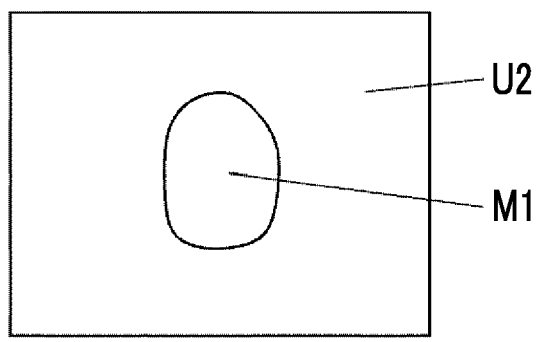
FIG. 5 is a diagram schematically illustrating an example of a pseudo orthogonal cross-sectional image.

The pseudo orthogonal cross section generation unit 26 generates a pseudo orthogonal cross-sectional image U2 orthogonal to an observation plane as illustrated in FIG. 5 by setting a cross section extraction line L1 passing through a lesion part M1 on one frame image U1 of a plurality of frame images U1 constituting a video stored in the image memory 24 as illustrated in FIG. 4 and arranging, in time series, pixel values on the cross section extraction line L1 in the plurality of frame images U1 constituting the video, for example, arranging, in time series, pixel values from the frame image U1 acquired in the past to the latest frame image U1.

For example, the pseudo orthogonal cross section generation unit 26 can set the cross section extraction line L1 on the frame image U1 with the largest lesion part M1 detected by the lesion detection unit 25, among the plurality of frame images U1.

Further, for example, the pseudo orthogonal cross section generation unit 26 can set the cross section extraction line L1 on one frame image U1 designated by the user via the input device 30, among the plurality of frame images U1.

The pseudo orthogonal cross section generation unit 26 can track the position of the lesion part M1 included in each of the plurality of frame images U1 on the basis of the detection result of the lesion part M1 by the lesion detection unit 25, and set the cross section extraction lines L1 for the lesion parts M1 of the plurality of frame images U1 to have the same positional relationship as the positional relationship between the lesion part M1 and the cross section extraction line L1 of one frame image U1. The pseudo orthogonal cross section generation unit 26 can arrange, in time series, the pixel values on the cross section extraction lines L1 of the plurality of frame images U1 set in this manner.

Here, since the pseudo orthogonal cross-sectional image U2 is generated by simply arranging, in time series, the pixel values on the cross section extraction lines L1 in the plurality of frame images U1, for example, in a case where the speed at which the user moves the ultrasound probe 10 at the time of capturing the plurality of frame images U1 fluctuates, that is, in a case where the ultrasound probe 10 is not moving at a constant speed, the temporal intervals between pixels in the horizontal direction orthogonal to the depth direction are not constant, and therefore, the structure of the lesion part M1 may not be correctly reproduced.

Figure 6:
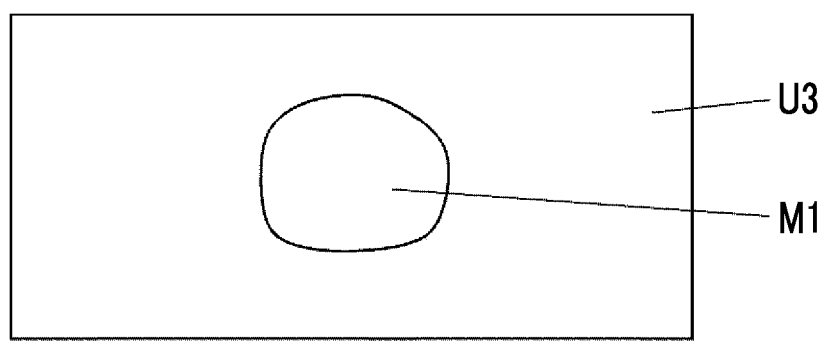
FIG. 6 is a diagram schematically illustrating an example of a normalized pseudo orthogonal cross-sectional image.

Then, in order to improve the accuracy of the cross-sectional image of the lesion part M1, the pseudo orthogonal cross section deformation unit 27 non-rigidly deforms the pseudo orthogonal cross-sectional image U2 in the horizontal direction to generate a normalized pseudo orthogonal cross-sectional image U3 in a case where the scanning speed of the ultrasound probe 10 is made constant as illustrated in FIG. 6. The normalized pseudo orthogonal cross-sectional image U3 includes the lesion part M1 of which the structure is accurately reproduced. Here, the horizontal direction refers to a direction orthogonal to the depth direction in the pseudo orthogonal cross-sectional image U2.

Figure 7:
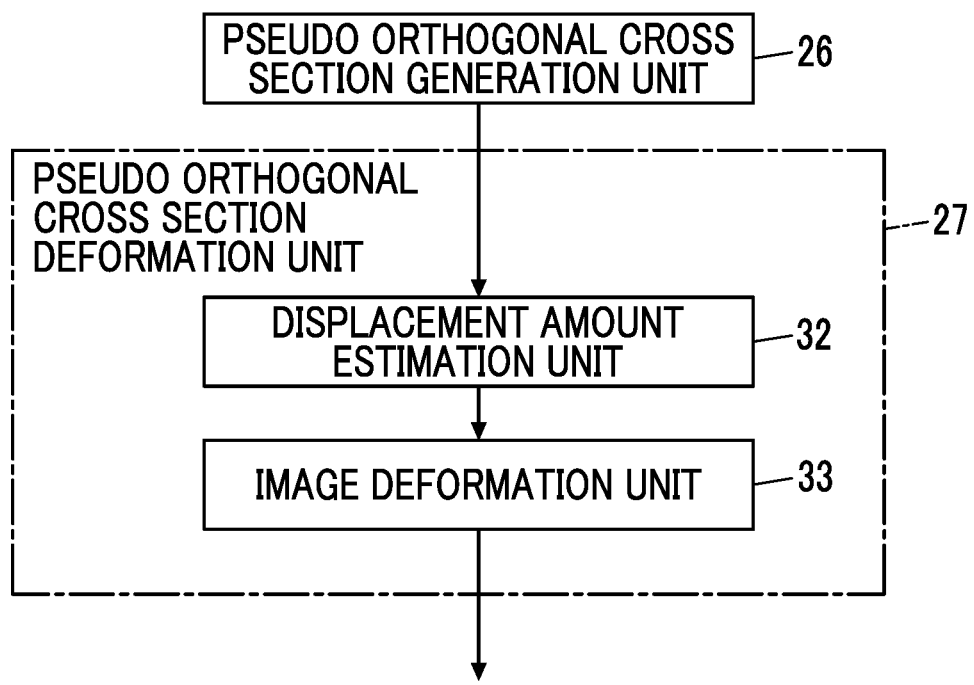
FIG. 7 is a block diagram illustrating an internal configuration of a pseudo orthogonal cross section deformation unit in the first embodiment.

As illustrated in FIG. 7, the pseudo orthogonal cross section deformation unit 27 includes a displacement amount estimation unit 32 and an image deformation unit 33.

The displacement amount estimation unit 32 estimates a displacement amount between a position of the pixel in the pseudo orthogonal cross-sectional image U2 in a case where the scanning speed of the ultrasound probe 10 is made constant and a position of the pixel in the actual pseudo orthogonal cross-sectional image U2 for each of time points at which the plurality of frame images U1 are captured, that is, corresponding to each of the plurality of frame images U1. For example, the displacement amount estimation unit 32 can include a displacement amount estimation model using a so-called neural network in which H and T are positive integer values, the pseudo orthogonal cross-sectional image U2 consisting of vertical H pixels and horizontal T pixels is input, and a displacement amount r(i) (i=1, 2, . . . , T) as T integer values is output, and the displacement amount estimation unit 32 can estimate the displacement amount r(i) by the displacement amount estimation model. The column number i of the pseudo orthogonal cross-sectional image U2 is a frame number of the plurality of frame images U constituting the video, and corresponds to a scanning time point of the pixel of the pseudo orthogonal cross-sectional image U2. Further, the displacement amount r(i) indicates a displacement amount between a position of the pixel in the pseudo orthogonal cross-sectional image U2 corresponding to the frame image U1 with the i-th frame number in a case where the scanning speed of the ultrasound probe 10 is made constant and an actual position of the pixel in the pseudo orthogonal cross-sectional image U2 corresponding to the frame image U1 with the i-th frame number. The displace amount represents how much the actual scanning position is displaced with respect to the column number i of the pseudo orthogonal cross-sectional image U2. Hereinafter, the column number i of the pseudo orthogonal cross-sectional image U2 can be referred to as a first column number i.

For example, the displacement amount estimation model can be trained for a relationship between the pseudo orthogonal cross-sectional image U2 and the displacement amount r(i) as follows. First, as training videos, videos generated by scanning at an arbitrary speed with the ultrasound probe, and probe position data X recorded by synchronizing the position of the ultrasound probe measured by a position sensor such as an acceleration sensor, a gyro sensor, or a magnetic sensor with the frame rate of the video are prepared. Here, the speed of the ultrasound probe at the time of generating the video may fluctuate. In a case where it is assumed that the number of frames of the video is N, the number of pieces of data of the probe position data X is also N. The pseudo orthogonal cross-sectional image U2 is generated by the pseudo orthogonal cross section generation unit 26 for the prepared video. Further, the probe position data X is converted into a displacement amount Y(t) (t=1, 2, . . . , M) by following Equation 1.

$$Y(t) = \text{Int}\left[\frac{X(t) - X(1)}{X(M) - X(1)} \times (M-1) + 1\right] - t \tag{1}$$

Here, t is a column number of the pseudo orthogonal cross-sectional image U2, that is, a frame number of the plurality of frame images U1 constituting the video. Further, "Int[ ]" is a function that truncates the decimal part of the numerical value in parentheses and outputs an integer value. The displacement amount Y(t) is a difference between the frame number of the pseudo orthogonal cross-sectional image that should be originally captured in a case where the ultrasound probe is moved at a constant speed, and the frame number of the pseudo orthogonal cross-sectional image U2 that is actually captured.

A large number of sets of the displacement amount Y(t) and the pseudo orthogonal cross-sectional image U2 obtained in this manner are prepared as teacher data, and the teacher data can be learned by the displacement amount estimation model by a learning method such as so-called back propagation method.

The image deformation unit 33 non-rigidly deforms the pseudo orthogonal cross-sectional image U2 in the horizontal direction to generate the normalized pseudo orthogonal cross-sectional image U3 such that a plurality of pixels corresponding to a plurality of positions arranged at equal intervals in the actual lesion part M1 are arranged at equal intervals in the horizontal direction of the image orthogonal to the depth direction, on the basis of the displacement amount r(i) estimated by the displacement amount estimation unit 32. The non-rigid deformation of the pseudo orthogonal cross-sectional image U2 performed by the image deformation unit 33 will be described later in detail.

The display controller 22 performs predetermined processing on the frame image U1 generated by the image generation unit 21, the normalized pseudo orthogonal cross-sectional image U3 generated by the pseudo orthogonal cross section deformation unit 27, and the like, and displays the processed images on the monitor 23.

The monitor 23 is for displaying the frame image U1 generated by the image generation unit 21, the normalized pseudo orthogonal cross-sectional image U3 generated by the pseudo orthogonal cross section deformation unit 27, and the like, under the control of the display controller 22, and includes, for example, a display device such as a liquid crystal display (LCD), or an organic electroluminescence (EL) display.

The main body controller 29 controls each unit of the apparatus main body 20 and the transmission and reception circuit 12 of the ultrasound probe 10 on the basis of a control program and the like stored in advance.

The input device 30 is for a user to perform an input operation, and is configured by, for example, a device such as a keyboard, a mouse, a trackball, a touchpad, and a touch sensor superimposed on the monitor 23.

The processor 31 having the image generation unit 21, the display controller 22, the lesion detection unit 25, the pseudo orthogonal cross section generation unit 26, the pseudo orthogonal cross section deformation unit 27, and the main body controller 29 is configured by a central processing unit (CPU) and a control program for causing the CPU to execute various kinds of processing, but the processor 31 may be configured by using a field programmable gate array (FPGA), a digital signal processor (DSP), an application specific integrated circuit (ASIC), a graphics processing unit (GPU), or other integrated circuits (IC) or may be configured by a combination thereof.

Further, the image generation unit 21, the display controller 22, the lesion detection unit 25, the pseudo orthogonal cross section generation unit 26, the pseudo orthogonal cross section deformation unit 27, and the main body controller 29 of the processor 31 can also be configured by being integrated partially or entirely into one CPU or the like.

Figure 8:
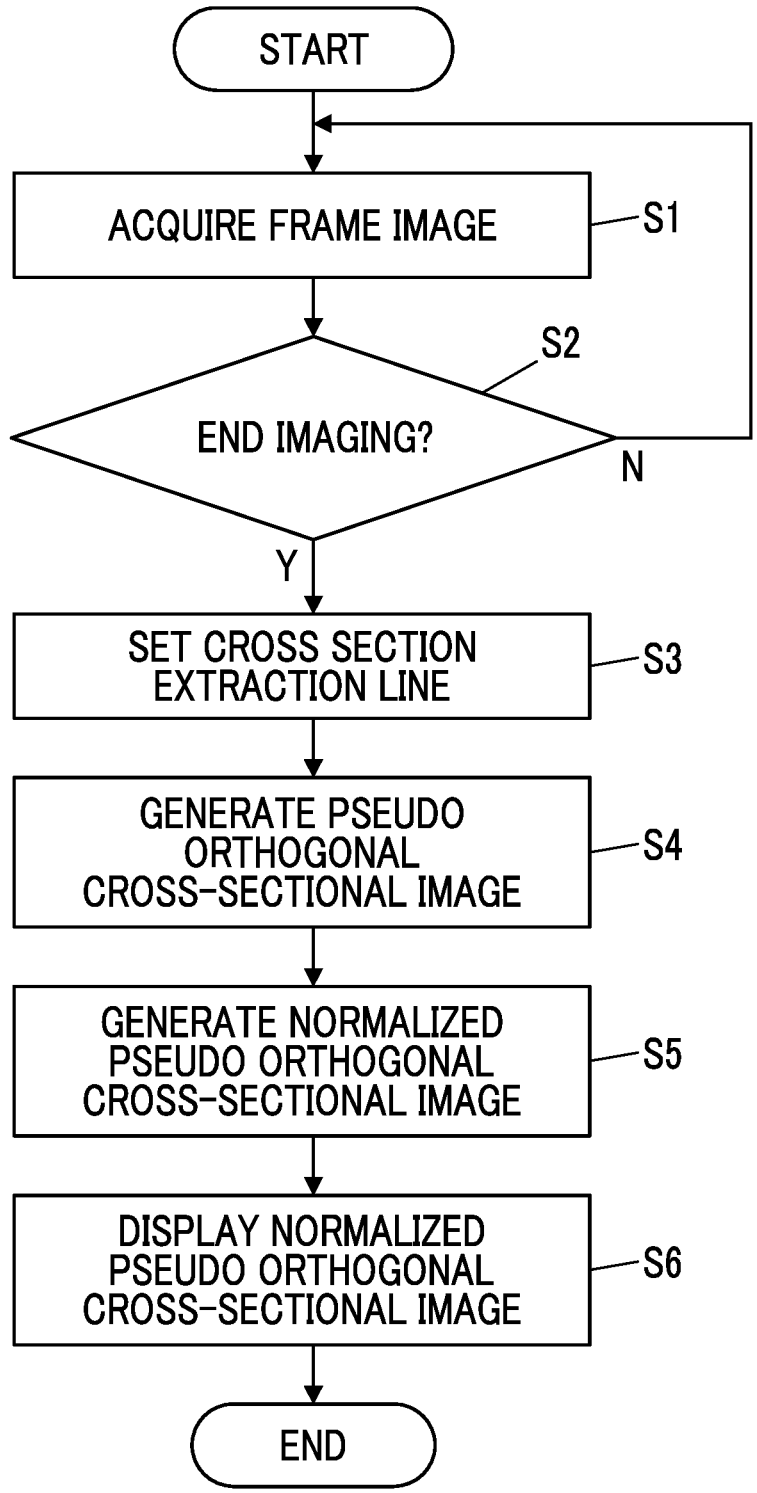
FIG. 8 is a flowchart illustrating an operation of the ultrasound diagnostic apparatus according to the first embodiment.

Next, the operation of the ultrasound diagnostic apparatus according to the first embodiment of the present invention will be described using the flowchart illustrated in FIG. 8.

First, in Step S1, in a state where the ultrasound probe 10 is in contact with the body surface of the subject by the user, the frame image U1 in which the lesion part M1 of the subject is imaged is acquired. In a case where the frame image U1 is acquired, the transmission and reception circuit 12 performs so-called reception focusing processing under the control of the main body controller 29 to generate sound ray signals. The sound ray signals generated by the transmission and reception circuit 12 are sent to the image generation unit 21. The image generation unit 21 generates the frame image U1 using the sound ray signals sent from the transmission and reception circuit 12. The frame image U1 acquired in this manner is sent to the image memory 24, and is stored in the image memory 24.

Next, in Step S2, the main body controller 29 determines whether to end the capturing of the frame image U1. For example, the main body controller 29 determines to end the capturing of the frame image U1 in a case where an instruction to end the capturing of the frame image U1 is input by the user via the input device 30. In this case, for example, the main body controller 29 controls each unit of the ultrasound diagnostic apparatus such as the transmission and reception circuit 12 to end the capturing of the frame image U1. For example, the main body controller 29 determines to continue the capturing of the frame image U1 in a case where an instruction to end the capturing of the frame image U1 is not input by the user via the input device 30, and causes each unit of the ultrasound diagnostic apparatus to continue the imaging.

In a case where it is determined not to end the capturing of the frame image U1 in Step S2, the processing returns to Step S1, and a new frame image U1 is acquired. In this manner, as long as it is determined not to end the capturing of the frame image U1 in Step S2, the processing of Step S1 and Step S2 is repeated, and the plurality of frame images U1 constituting the video are stored in the image memory 24. Further, in a case where it is determined to end the capturing of the frame image U1 in Step S2, the processing proceeds to Step S3.

In Step S3, the pseudo orthogonal cross section generation unit 26 sets the cross section extraction line L1 passing through, for example, the lesion part M1 as illustrated in FIG. 4 on one frame image U1 among the plurality of frame images U1 constituting the video, which are obtained by repeating Step S1 and Step S2.

For example, the pseudo orthogonal cross section generation unit 26 can set the cross section extraction line L1 passing through the lesion part M1 on the frame image U1 designated by the user via the input device 30. In Step S3, the lesion detection unit 25 can detect the lesion parts M1 in the plurality of frame images U1, and the pseudo orthogonal cross section generation unit 26 can set the cross section extraction line L1 on the frame image U1 including the largest lesion part M1 among the plurality of lesion parts M1 detected by the lesion detection unit 25.

For example, the pseudo orthogonal cross section generation unit 26 can set the cross section extraction line L1 for the lesion parts M1 in the plurality of frame images U1 such that the positional relationship between the set cross section extraction line L1 and the lesion part M1 is maintained.

Figure 9:
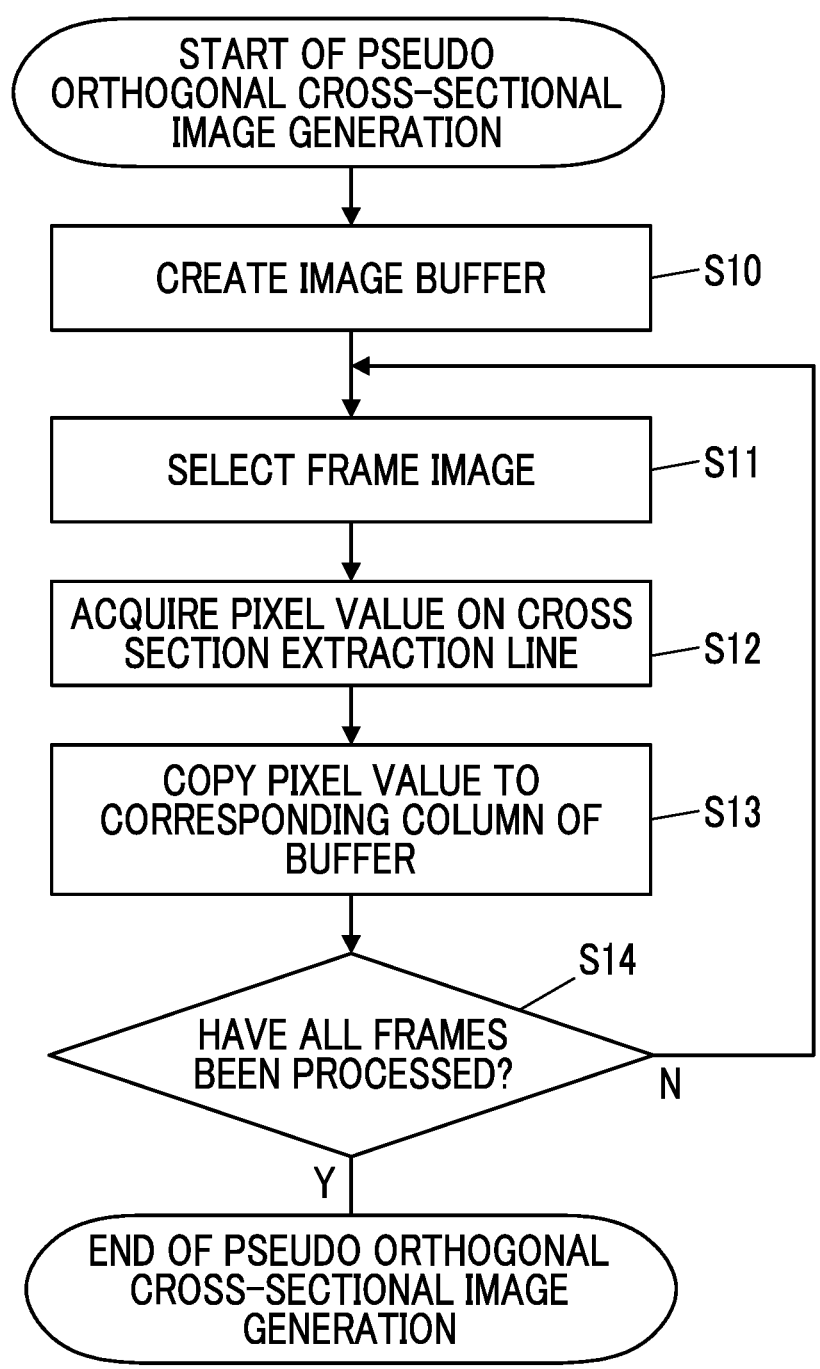
FIG. 9 is a flowchart illustrating an operation of generating a pseudo orthogonal cross-sectional image in the first embodiment.

In subsequent Step S4, the pseudo orthogonal cross section generation unit 26 generates the pseudo orthogonal cross-sectional image U2 orthogonal to the observation plane as illustrated in FIG. 5 by arranging, in time series, the pixel values on the same position as the position on the cross section extraction line L1 set in Step S3, in the plurality of frame images U1 constituting the video. The processing of Step S4 includes processing of Step S10 to Step S14 illustrated in the flowchart of FIG. 9.

First, in Step S10, the pseudo orthogonal cross section generation unit 26 creates an image buffer corresponding to the pseudo orthogonal cross-sectional image U2. The image buffer has a size of vertical H pixels and horizontal T1 pixels. Here, T1 is the number of frames of the plurality of frame images U1 constituting the video acquired by repeating Step S1 and Step S2, and is the number of pixels of the pseudo orthogonal cross-sectional image U2 in the horizontal direction.

In Step S11, the pseudo orthogonal cross section generation unit 26 selects the frame image U1, which is one of the plurality of frame images U1 constituting the video, for example, which is the oldest frame image U1, that is, of which the frame number is "1".

In Step S12, the pseudo orthogonal cross section generation unit 26 acquires the pixel value on the same position as the position on the cross section extraction line L1 set in Step S3, in the frame image U1 selected in Step S11.

In Step S13, the pseudo orthogonal cross section generation unit 26 copies the pixel value acquired in Step S12 to a column of the image buffer created in Step S10 corresponding to the frame image U1 selected in Step S11, for example, a column of the image buffer corresponding to the frame number "1".

In Step S14, the pseudo orthogonal cross section generation unit 26 determines whether or not the processing of Step S11 to Step S13 has been performed on all the plurality of frame images U1 constituting the video. At the current time point, since only the processing of Step S12 and Step S13 has been performed on one frame image U1, the pseudo orthogonal cross section generation unit 26 determines that the processing of Step S12 and Step S13 has not been performed on all the plurality of frame images U1 constituting the video. In this case, the processing returns to Step S11. In Step S11, the pseudo orthogonal cross section generation unit 26 selects the frame image U1 which has not been selected yet among the plurality of frame images U1 constituting the video, for example, the frame image U1 that is secondly acquired in the past.

In this manner, in Step S14, until it is determined that the processing of Step S12 and Step S13 has been performed on all the frame images U1 constituting the video, the processing of Step S11 to Step S14 is repeated. As a result, the pixel value is sequentially copied to the column of the image buffer created in Step S10.

In a case where it is determined in Step S14 that the processing of Step S12 and Step S13 has been performed on all the frame images U1 constituting the video, the processing of Step S4 is completed. As a result, the pixel values on the cross section extraction line L1 in the corresponding frame image U1 are copied to all columns of the image buffer created in Step S10, and the pseudo orthogonal cross-sectional image U2 is generated.

Figure 10:
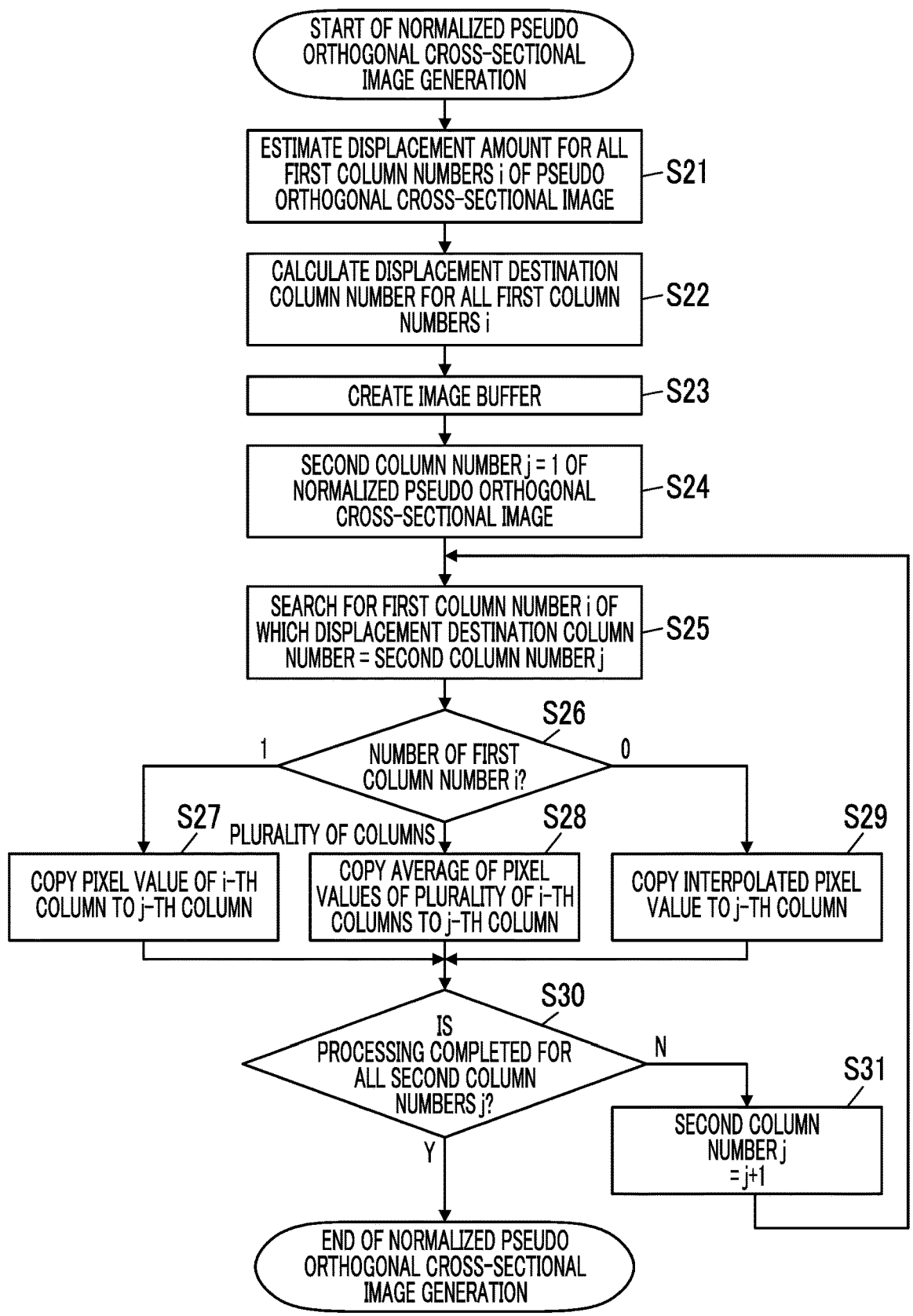
FIG. 10 is a flowchart illustrating an operation of generating a normalized pseudo orthogonal cross-sectional image in the first embodiment.

In a case where Step S4 is completed in this manner, the processing proceeds to Step S5. In Step S5, the pseudo orthogonal cross section deformation unit 27 non-rigidly deforms the pseudo orthogonal cross-sectional image U2 generated in Step S4 in the horizontal direction to generate the normalized pseudo orthogonal cross-sectional image U3 in a case where the scanning speed of the ultrasound probe 10 is made constant. The processing of Step S5 includes processing of Step S21 to Step S31 illustrated in the flowchart of FIG. 10.

In Step S21, the pseudo orthogonal cross section deformation unit 27 estimates the displacement amount r(i) for all the first column numbers i of the pseudo orthogonal cross-sectional image U2 generated in Step S4. In this case, the pseudo orthogonal cross section deformation unit 27 can estimate the displacement amount r(i) by using the displacement amount estimation model trained for the relationship between the pseudo orthogonal cross-sectional image U2 and the displacement amount r(i), for example. For example, the displacement amount estimation model can be trained using a plurality of sets of the pseudo orthogonal cross-sectional image U2 and the displacement amount Y(t) represented by Equation (1) as teacher data.

In Step S22, the pseudo orthogonal cross section deformation unit 27 calculates a displacement destination column number for all the first column numbers i of the pseudo orthogonal cross-sectional image U2. Here, the displacement destination column number is calculated by adding or subtracting a constant to the sum i+r(i) of the first column number i and the displacement amount r(i) estimated in Step S21 such that 1+r(1) is 1. Table 1 below illustrates examples of the first column number i, the displacement amount r(i), the sum i+r(i), and the displacement destination column number of the pseudo orthogonal cross-sectional image U2. In the example of Table 1, sine 1+r(1)=−4, the displacement destination column number is calculated by adding a constant 5 to the sum i+r(i).

TABLE 1

| FIRST COLUMN NUMBER i | DISPLACEMENT AMOUNT r(i) | SUM i + r(i) | DISPLACEMENT DESTINATION COLUMN NUMBER |
|---|---|---|---|
| 1 | −5 | −4 | 1 |
| 2 | −4 | −2 | 3 |
| 3 | −2 | 1 | 6 |
| 4 | 0 | 4 | 9 |
| 5 | 1 | 6 | 11 |
| 6 | 0 | 6 | 11 |
| 7 | 3 | 10 | 15 |
| ... | ... | ... | ... |
| T1 | 10 | T1 + 10 | T1 + 15 |

In Step S23, the pseudo orthogonal cross section deformation unit 27 creates an image buffer corresponding to the normalized pseudo orthogonal cross-sectional image U3. The image buffer has a size of vertical H pixels and horizontal T2 pixels. Here, T2 is a number obtained by adding 1 to the difference between the maximum value and the minimum value of the displacement destination column number. In the example of Table 1, T2=T1+15.

In Step S24, the pseudo orthogonal cross section deformation unit 27 selects the column number j=1 of the normalized pseudo orthogonal cross-sectional image U3. Hereinafter, the column number j of the normalized pseudo orthogonal cross-sectional image U3 is referred to as a second column number j.

In Step S25, the pseudo orthogonal cross section deformation unit 27 searches for the first column number i of which the displacement destination column number calculated in Step S22 is equal to the second column number j selected in Step S24. In the example of Table 1, the pseudo orthogonal cross section deformation unit 27 can search for the first column number i=1 of which the displacement destination column number is the second column number j=1.

In Step S26, the pseudo orthogonal cross section deformation unit 27 determines the number of first column numbers i searched in Step S25. The processing proceeds to Step S27 in a case where the number of searched first column numbers i is one, the processing proceeds to Step S28 in a case where the number of searched first column numbers i is plural, and the processing proceeds to Step S29 in a case where the number of searched first column numbers i is zero.

In the example of Table 1, since the number of first column numbers i searched in Step S25 is one of "1" in the case of the second column number j=1, the processing proceeds to Step S27. In Step S27, the pseudo orthogonal cross section deformation unit 27 copies the pixel value of the first column number i=1 of the pseudo orthogonal cross-sectional image U2 to the column of the image buffer created in Step S23 of which the second column number j is 1.

In Step S30 subsequent to Step S27, the pseudo orthogonal cross section deformation unit 27 determines whether or not the processing of Step S26 to Step S29 has been completed for all the second column numbers j. In a case where it is determined that the processing has not been completed for all the second column numbers j, the processing proceeds to Step S31.

In Step S31, the pseudo orthogonal cross section deformation unit 27 selects a number obtained by adding 1 to the second column number j=1 that is currently selected, that is, the second column number j=2. In a case where Step S31 is completed, the processing returns to Step S25.

In Step S25, the pseudo orthogonal cross section deformation unit 27 searches for the first column number i of which the displacement destination column number=the second column number j=2. In the example of Table 1, since there is no "2" in the displacement destination column number, in this case, the first column number i cannot be searched in Step S25. In a case where the scanning speed of the ultrasound probe 10 is suddenly increased while the plurality of frame images U1 are captured, the displacement amount r(i) is increased, and the first column number i of which the displacement destination column number=the second column number j is not searched in some cases.

In Step S26, in a case where it is determined that the number of first column numbers i searched in Step S25 is zero, the processing proceeds to Step S29. In Step S29, the pseudo orthogonal cross section deformation unit 27 interpolates the pixel value, and copies the interpolated pixel value to the column of the image buffer created in Step S23 of which the second column number j is 2. In this case, for example, the pseudo orthogonal cross section deformation unit 27 can interpolate pixel values between the pixel value of the first column number i=1 and the pixel value of the first column number i=3 corresponding to two displacement destination column numbers closest to the displacement destination column number that has not been searched, for example, two displacement destination column numbers "1" and "3" closest to the displacement destination column number=the second column number j=2, and copy the pixel value obtained by the interpolation to the column of the image buffer of which the second column number j is 2. The interpolation method is not particularly limited, and for example, a known method such as so-called linear interpolation or quadratic interpolation can be used.

In Step S30 subsequent to Step S28, the pseudo orthogonal cross section deformation unit 27 determines whether or not the processing of Step S25 to Step S29 has been completed for all the second column numbers j, and the processing proceeds to Step S31 in a case where it is determined that the processing has not been completed for all the second column numbers j.

In Step S31, 1 is added to the second column number j. Thereafter, the processing returns to Step S25.

Step S25 to Step S31 are repeated in this manner, and in a case where the second column number j=11 is selected in Step S31, the first column number i of which the displacement destination column number=the second column number j=11 is searched in subsequent Step S25. In the example of Table 1, there are two first column numbers i "5" and "6" of which the displacement destination column number=the second column number j=11, and the first column numbers i=5 and 6 are searched. While the plurality of frame images U1 are captured, for example, in a case where the ultrasound probe 10 is paused or the like, the plurality of first column numbers i are searched.

In subsequent Step S25, it is determined that the number of searched first column numbers i is two (plural) of "5" and "6", and the processing proceeds to Step S28.

In Step S28, the pseudo orthogonal cross section deformation unit 27 copies the average value of the pixel values of the plurality of searched first column numbers i to the column of the image buffer corresponding to the second column number j. In the example of Table 1, the pseudo orthogonal cross section deformation unit 27 copies the average value of the pixel values of the searched first column numbers i=5 and 6 to the column of the image buffer of which the second column number j is 11, for example.

In this manner, by repeating the processing of Step S25 to Step S31, the pixel values are sequentially copied to the columns of the image buffer created in Step S23.

In Step S30, in a case where it is determined that the processing of Step S25 to Step S29 has been completed for all the second column numbers j, the processing of Step S5 is completed. As a result, the pixel values are copied to all columns of the image buffer created in Step S23, and the normalized pseudo orthogonal cross-sectional image U3 is generated. The normalized pseudo orthogonal cross-sectional image U3 represents a cross-sectional image of the lesion part M1 in a case where the scanning speed of the ultrasound probe 10 is made constant. With the processing of Step S5, a cross-sectional image with high accuracy is obtained.

Finally, in Step S6, the normalized pseudo orthogonal cross-sectional image U3 generated in Step S5 is displayed on the monitor 23. In this case, for example, the frame image U1 can be displayed on the monitor 23 together with the normalized pseudo orthogonal cross-sectional image U3 by the user's input operation via the input device 30. The user can accurately diagnose the lesion part M1 of the subject by checking the normalized pseudo orthogonal cross-sectional image U3 displayed on the monitor 23.

As described above, with the ultrasound diagnostic apparatus of the first embodiment, the pseudo orthogonal cross section generation unit 26 generates the pseudo orthogonal cross-sectional image U2 orthogonal to the observation plane by arranging, in time series, the pixel values on the cross section extraction line L1 in the plurality of frame images U1 constituting the video, and the pseudo orthogonal cross section deformation unit 27 non-rigidly deforms the pseudo orthogonal cross-sectional image U2 in the horizontal direction to generate the normalized pseudo orthogonal cross-sectional image U3 in a case where the scanning speed of the ultrasound probe 10 is made constant. Therefore, it is possible to obtain the cross-sectional image in which the structure of the lesion part M1 is accurately reproduced.

It has been described that the ultrasound probe 10 and the apparatus main body 20 are connected to each other in a wired manner, but the ultrasound probe 10 and the apparatus main body 20 can be connected to each other in a wireless manner.

The apparatus main body 20 may be a so-called stationary type, a portable type, or a handheld type configured by a so-called smartphone or tablet computer. As described above, the type of equipment constituting the apparatus main body 20 is not particularly limited.

Further, the transmission and reception circuit 12 is included in the ultrasound probe 10, but the transmission and reception circuit 12 may be included in the apparatus main body 20 instead of being included in the ultrasound probe 10.

Further, the image generation unit 21 is included in the apparatus main body 20, but the image generation unit 21 may be included in the ultrasound probe 10 instead of being included in the apparatus main body 20.

In a case of setting the cross section extraction line L1 passing through the lesion part M1, the pseudo orthogonal cross section generation unit 26 can set the cross section extraction line L1 at a position determined for the lesion part M1, such as the center of the lesion part M1 or a position where the width of the lesion part M1 is internally divided at a constant ratio. In this manner, the position of the lesion part M1 through which the cross section extraction line L1 is set to pass can be decided by the user's input operation via the input device 30 or can be unchangeably decided for each apparatus.

It has been described that the pseudo orthogonal cross section deformation unit 27 non-rigidly deforms the pseudo orthogonal cross-sectional image U2 in the horizontal direction to generate the normalized pseudo orthogonal cross-sectional image U3, but in this case, the pseudo orthogonal cross section deformation unit 27 can non-rigidly deform the pseudo orthogonal cross-sectional image U2 in the depth direction as necessary.

Second Embodiment

In the first embodiment, the pseudo orthogonal cross section deformation unit 27 estimates the displacement amount r(i) using the displacement amount estimation model, but can estimate the displacement amount r(i) on the basis of the signal from the motion sensor attached to the ultrasound probe 10.

Figure 11:
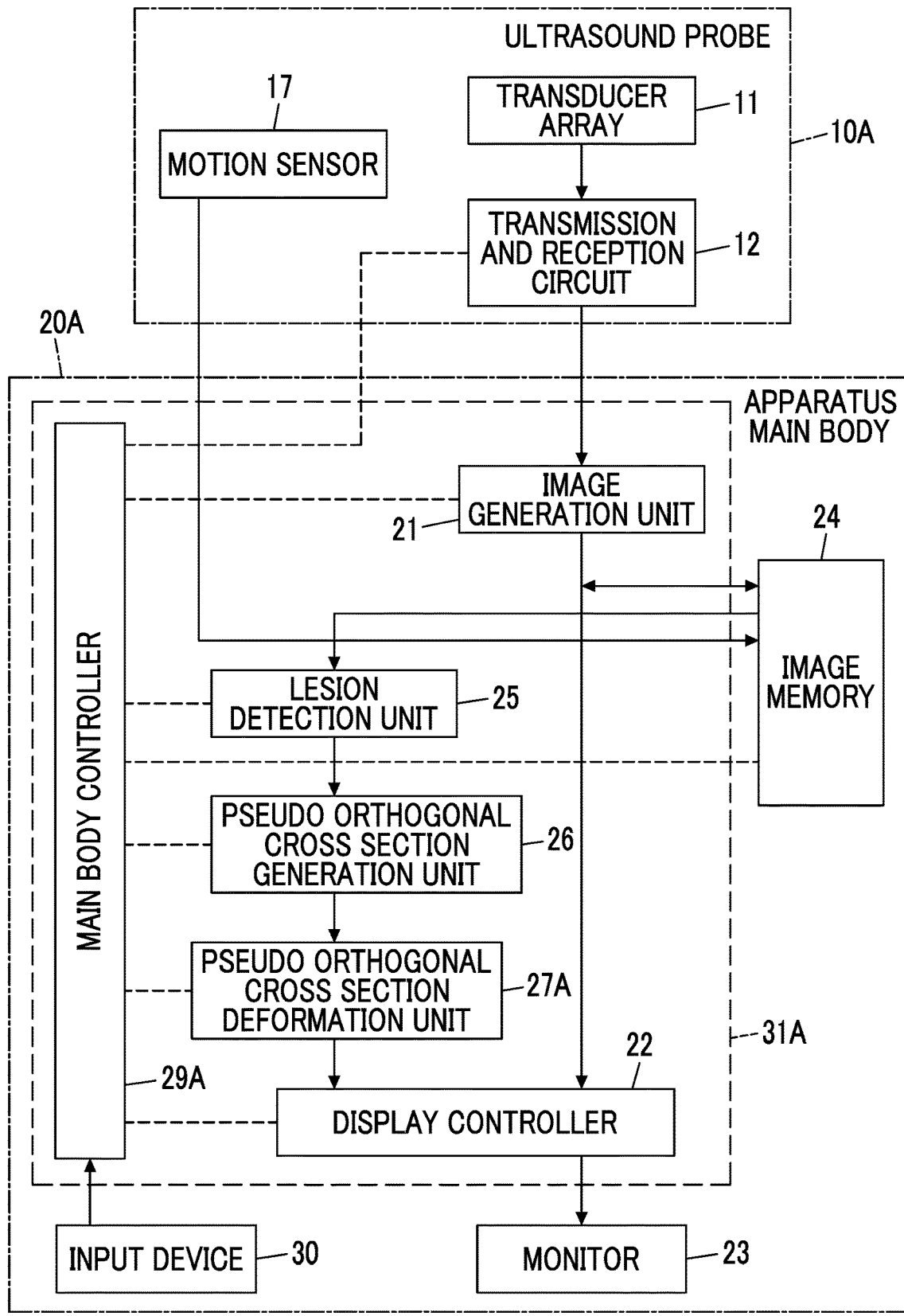
FIG. 11 is a block diagram illustrating a configuration of an ultrasound diagnostic apparatus according to a second embodiment.

FIG. 11 illustrates a configuration of an ultrasound diagnostic apparatus of a second embodiment. The ultrasound diagnostic apparatus of the second embodiment is obtained by including an ultrasound probe 10A instead of the ultrasound probe 10 and including an apparatus main body 20A instead of the apparatus main body 20 in the ultrasound diagnostic apparatus of the first embodiment illustrated in FIG. 1.

The ultrasound probe 10A is obtained by adding a motion sensor 17 to the ultrasound probe 10 in the first embodiment. The motion sensor 17 is connected to the image memory 24.

Figure 12:
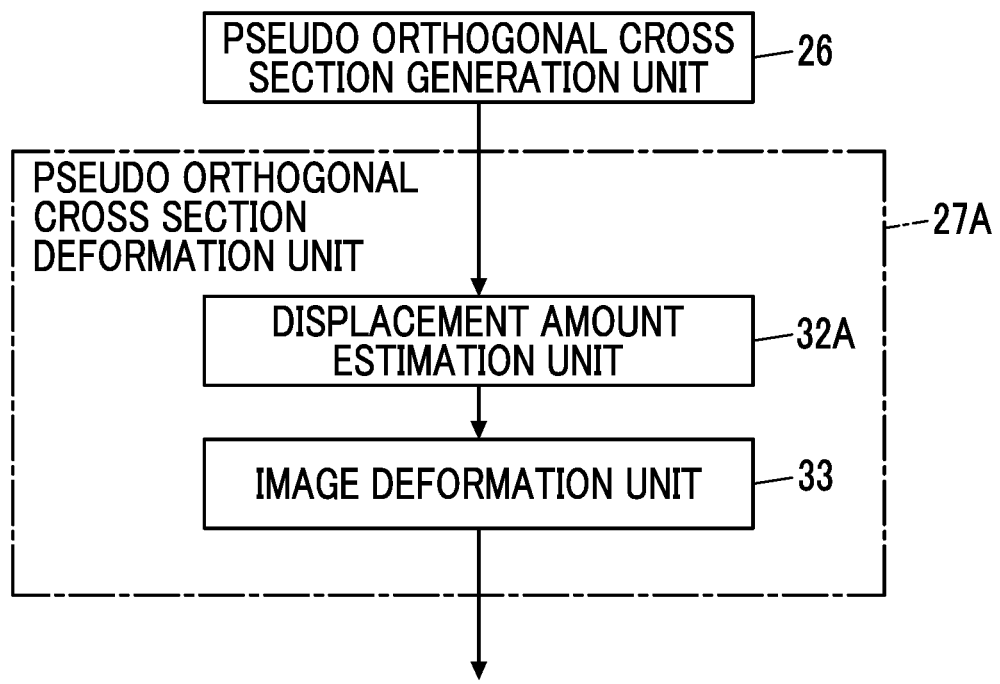
FIG. 12 is a block diagram illustrating an internal configuration of a pseudo orthogonal cross section deformation unit in the second embodiment.

The apparatus main body 20A is obtained by including a pseudo orthogonal cross section deformation unit 27A instead of the pseudo orthogonal cross section deformation unit 27 and including a main body controller 29A instead of the main body controller 29 in the apparatus main body 20 in the first embodiment. As illustrated in FIG. 12, the pseudo orthogonal cross section deformation unit 27A includes a displacement amount estimation unit 32A instead of the displacement amount estimation unit 32 in the pseudo orthogonal cross section deformation unit 27 in the first embodiment.

Further, the image generation unit 21, the display controller 22, the lesion detection unit 25, the pseudo orthogonal cross section generation unit 26, the pseudo orthogonal cross section deformation unit 27A, and the main body controller 29A constitute a processor 31A for the apparatus main body 20A.

The motion sensor 17 is a sensor device that is attached to the ultrasound probe 10A, and detects a moving speed of the ultrasound probe 10A. The motion sensor 17 sends the moving speed of the ultrasound probe 10A to the image memory 24 in synchronization with the generation frame rate of the frame image U1 generated by the image generation unit 21. The moving speed of the ultrasound probe 10A sent to the image memory 24 in this manner is stored as a moving speed V(i) (i=1, 2, . . . , T) in the image memory 24 by being associated with each of the plurality of corresponding frame images U1.

For example, the motion sensor 17 can include a known sensor device such as an acceleration sensor, an angular velocity sensor, or a magnetic sensor.

The displacement amount estimation unit 32A of the pseudo orthogonal cross section deformation unit 27A estimates the displacement amount r(i) on the basis of the moving speed V(i) of the ultrasound probe 10A detected by the motion sensor 17. Specifically, the pseudo orthogonal cross section deformation unit 27A can estimate the displacement amount r(i) corresponding to the first column number i of the pseudo orthogonal cross-sectional image U2 by using Equation (2) and Equation (3) described below.

$$r(i) = \text{Int}\left[\frac{\sum_{j=1}^{i} V(j) - \overline{V} \times i}{\overline{V}}\right] \times T \qquad (2)$$

$$\overline{V} = \frac{\sum_{j=1}^{T} V(j)}{T} \qquad (3)$$

The image deformation unit 33 non-rigidly deforms the pseudo orthogonal cross-sectional image U2 in the horizontal direction on the basis of the displacement amount r(i) estimated by the displacement amount estimation unit 32A in this manner to generate the normalized pseudo orthogonal cross-sectional image U3 in a case where the scanning speed of the ultrasound probe 10A is made constant.

As described above, with the ultrasound diagnostic apparatus of the second embodiment, even in a case where the displacement amount estimation unit 32A estimates the displacement amount r(i) by using Equation (2) and Equation (3) using the moving speed V(i) of the ultrasound probe 10A measured by the motion sensor 17, the normalized pseudo orthogonal cross-sectional image U3 in which the structure of the lesion part M1 is accurately reproduced is obtained.

Third Embodiment

In the embodiment of the present invention, since the normalized pseudo orthogonal cross-sectional image U3 in which the structure of the lesion part M1 is accurately reproduced is obtained, the size and the like of the lesion part M1 can be accurately measured by using the normalized pseudo orthogonal cross-sectional image U3.

Figure 13:
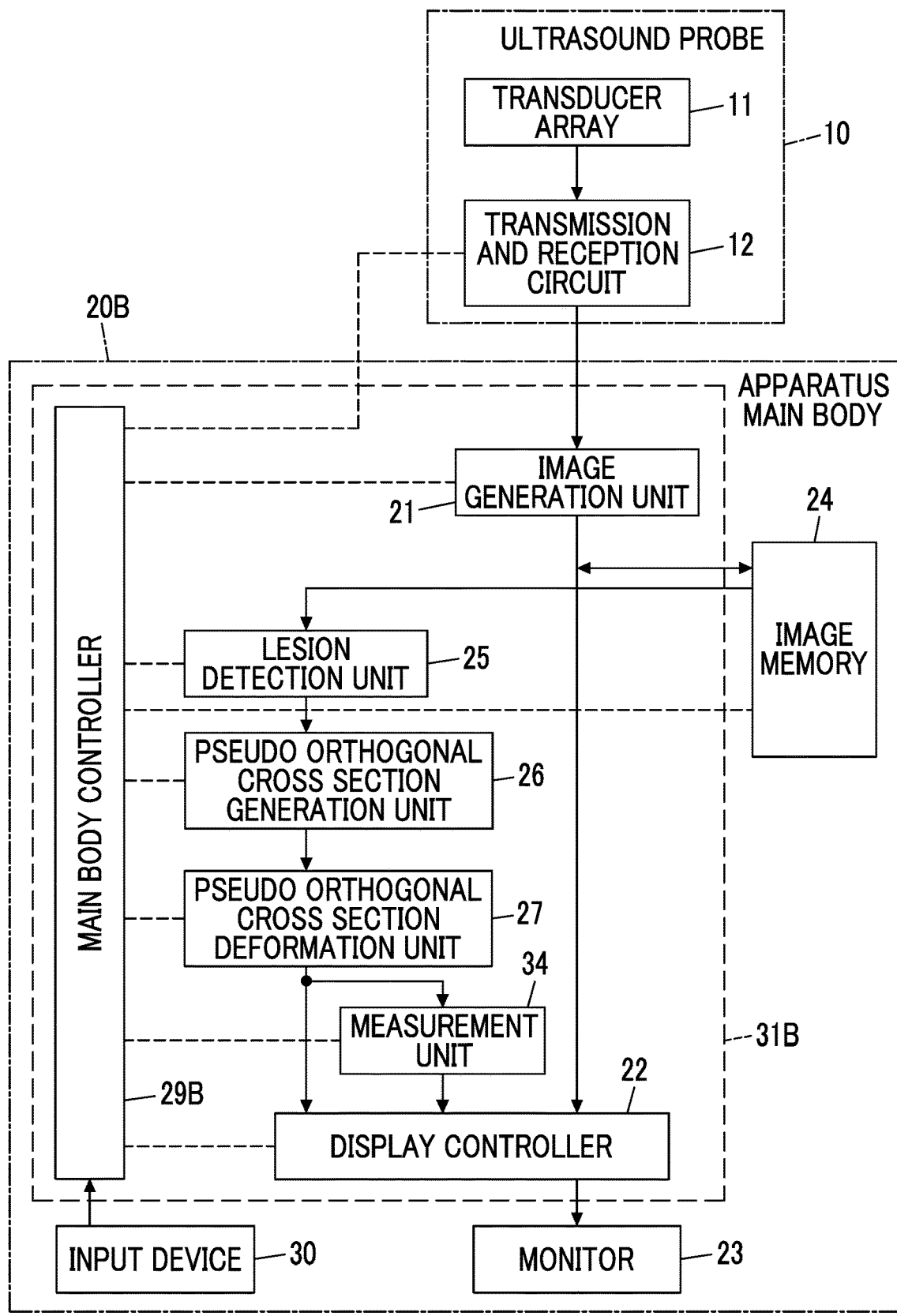
FIG. 13 is a block diagram illustrating a configuration of an ultrasound diagnostic apparatus according to a third embodiment.

FIG. 13 illustrates a configuration of an ultrasound diagnostic apparatus of a third embodiment. The ultrasound diagnostic apparatus of the third embodiment is obtained by including an apparatus main body 20B instead of the apparatus main body 20 in the ultrasound diagnostic apparatus of the first embodiment illustrated in FIG. 1.

The apparatus main body 20B is obtained by adding a measurement unit 34 and including a main body controller 29B instead of the main body controller 29 in the apparatus main body 20 in the first embodiment. The measurement unit 34 is connected to the display controller 22, the pseudo orthogonal cross section deformation unit 27, and the main body controller 29B.

Further, the image generation unit 21, the display controller 22, the lesion detection unit 25, the pseudo orthogonal cross section generation unit 26, the pseudo orthogonal cross section deformation unit 27, the main body controller 29B, and the measurement unit 34 constitute a processor 31B for the apparatus main body 20B.

The measurement unit 34 detects the lesion part M1 from the normalized pseudo orthogonal cross-sectional image U3 generated by the pseudo orthogonal cross section deformation unit 27, and measures the size of the lesion part M1. For example, the measurement unit 34 can detect the lesion part M1 using a lesion detection algorithm described in "REDMON, Joseph, et al. You only look once: Unified, real-time object detection. In: Proceedings of the IEEE conference on computer vision and pattern recognition. 2016. p. 779-788".

Further, for example, the measurement unit 34 can detect the lesion part M1 by a so-called template matching method of storing a plurality of template images regarding the lesion part M1, and using these template images. For example, the measurement unit 34 can detect the lesion part M1 by using a machine learning method described in Csurka et al.: Visual Categorization with Bags of Keypoints, Proc. of ECCV Workshop on Statistical Learning in Computer Vision, pp. 59-74 (2004), or a general image recognition method using deep learning described in Krizhevsk et al.: ImageNet Classification with Deep Convolutional Neural Networks, Advances in Neural Information Processing Systems 25, pp. 1106-1114 (2012).

The measurement unit 34 can particularly measure the size of the lesion part M1 in the horizontal direction orthogonal to the depth direction in a case of measuring the size of the lesion part M1 included in the normalized pseudo orthogonal cross-sectional image U3. As a result, it is possible to accurately obtain the size of the lesion part M1 in the scanning direction, that is, in the movement direction of the ultrasound probe 10.

As described above, with the ultrasound diagnostic apparatus of the third embodiment, since the size of the lesion part M1 in the scanning direction can be accurately measured from the normalized pseudo orthogonal cross-sectional image U3, the user such as a doctor can smoothly and precisely perform an examination for the lesion part M1 without requiring to newly capture the frame image U1 by changing the orientation of the ultrasound probe 10 in order to measure the size of the lesion part M1 in the scanning direction.

The measurement of the size of the lesion part M1 has been described, but the measurement unit 34 can measure the volume of the lesion part M1.

In this case, first, the pseudo orthogonal cross section generation unit 26 sets a plurality of cross section extraction lines L1 extending in parallel to each other and passing through the lesion part M1 in one frame image U1, and generates a plurality of pseudo orthogonal cross-sectional images U2. Next, the pseudo orthogonal cross section deformation unit 27 generates a plurality of normalized pseudo orthogonal cross-sectional images U3 on the basis of the plurality of pseudo orthogonal cross-sectional images U2 generated by the pseudo orthogonal cross section generation unit 26. The measurement unit 34 can measure the number of pixels, that is, the area of the lesion part M1 from each of the plurality of normalized pseudo orthogonal cross-sectional images U3 generated by the pseudo orthogonal cross section deformation unit 27, and calculate the volume of the lesion part M1 by adding the obtained values of the plurality of areas.

Fourth Embodiment

In some cases, the user such as a doctor determines the malignancy grade of the lesion part M1 by checking the image in which the lesion part M1 is imaged. The ultrasound diagnostic apparatus of the embodiment of the present invention can calculate the malignancy grade of the lesion part M1 by analyzing the image in which the lesion part M1 is imaged.

Figure 14:
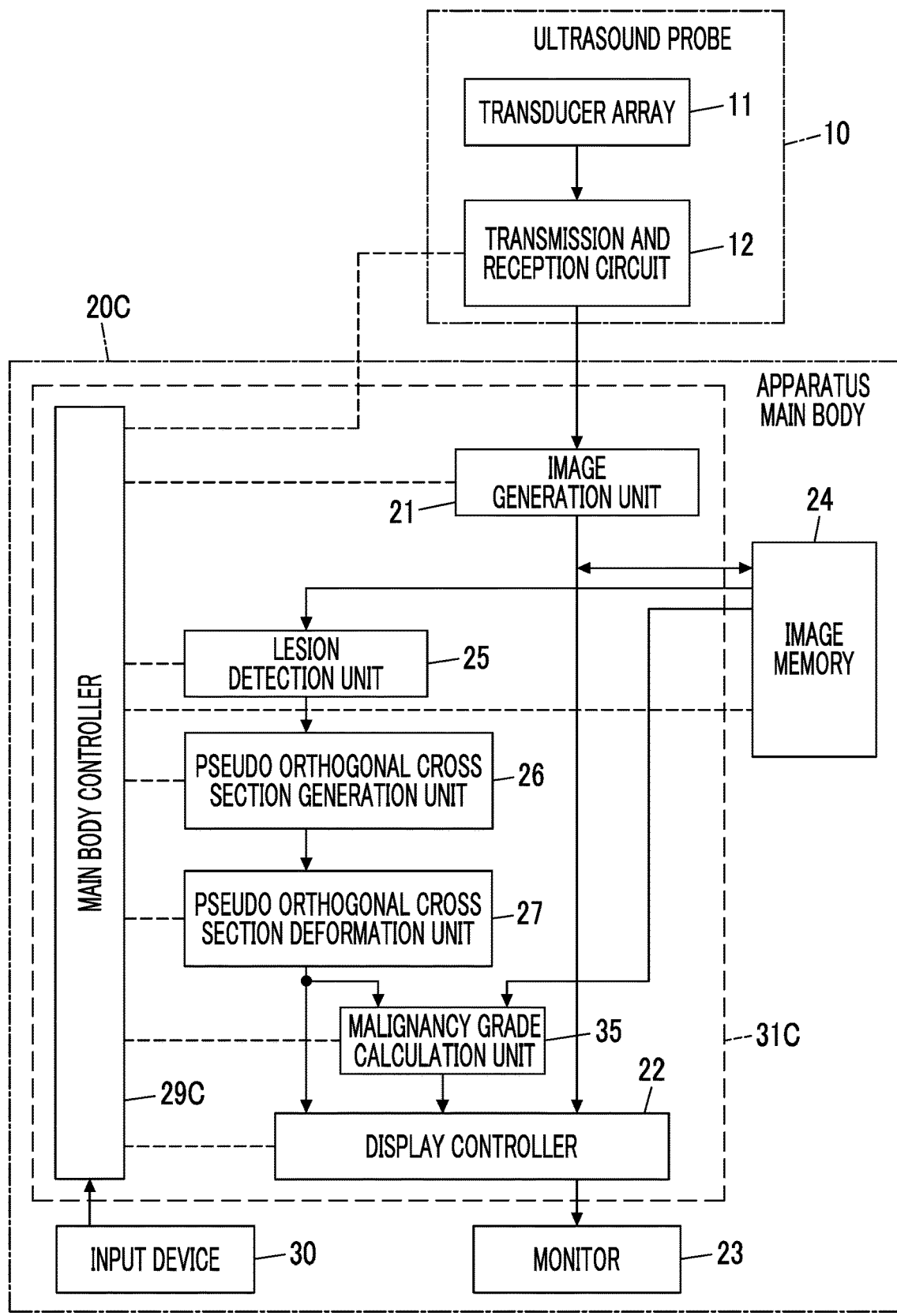
FIG. 14 is a block diagram illustrating a configuration of an ultrasound diagnostic apparatus according to a fourth embodiment.

FIG. 14 illustrates a configuration of an ultrasound diagnostic apparatus of a fourth embodiment. The ultrasound diagnostic apparatus of the fourth embodiment is obtained by including an apparatus main body 20C instead of the apparatus main body 20 in the ultrasound diagnostic apparatus of the first embodiment illustrated in FIG. 1.

The apparatus main body 20C is obtained by adding a malignancy grade calculation unit 35 and including a main body controller 29C instead of the main body controller 29 in the apparatus main body 20 in the first embodiment. The malignancy grade calculation unit 35 is connected to the display controller 22, the image memory 24, the pseudo orthogonal cross section deformation unit 27, and the main body controller 29C. Further, the image generation unit 21, the display controller 22, the lesion detection unit 25, the pseudo orthogonal cross section generation unit 26, the pseudo orthogonal cross section deformation unit 27, the main body controller 29C, and the malignancy grade calculation unit 35 constitute a processor 31C for the apparatus main body 20C.

The malignancy grade calculation unit 35 calculates the malignancy grade of the lesion part M1 on the basis of the image in which the lesion part M1 is imaged. For example, the malignancy grade calculation unit 35 can have a malignancy grade calculation model that is trained in advance for a large number of sets consisting of images in each of which the lesion part M1 is imaged and the malignancy grades of the lesion parts M1 shown in the images, as teacher data. In this case, the malignancy grade calculation unit 35 can calculate the malignancy grade of the lesion part M1 by inputting the image in which the lesion part M1 is imaged, to the malignancy grade calculation model.

The malignancy grade of the lesion part M1 calculated by the malignancy grade calculation unit 35 is displayed on the monitor 23 via the display controller 22. The user such as a doctor can precisely and easily diagnose the lesion part M1 by checking the value of the malignancy grade displayed on the monitor 23.

Further, the malignancy grade calculation unit 35 can calculate a first malignancy grade of the lesion part M1 on the basis of one of the plurality of frame images U1 constituting the video, calculate a second malignancy grade of the lesion part M1 on the basis of the normalized pseudo orthogonal cross-sectional image U3 generated by the pseudo orthogonal cross section deformation unit 27, and calculate a total malignancy grade obtained by integrating the first malignancy grade and the second malignancy grade. Here, the frame image U1 used for calculating the first malignancy grade can be read from the image memory 24 by the user's instruction via the input device 30, for example.

In the normalized pseudo orthogonal cross-sectional image U3, the structure of the lesion part M1 is accurately reproduced, and therefore, the second malignancy grade can be accurately calculated. The total malignancy grade is calculated on the basis of two cross sections of the lesion part M1, which are orthogonal to each other, and therefore, a more accurate value than the first malignancy grade and the second malignancy grade is obtained. Therefore, the user such as a doctor can precisely and easily diagnose the lesion part M1 by checking the total malignancy grade displayed on the monitor 23.

EXPLANATION OF REFERENCES

- 10, 10A: ultrasound probe
- 11: transducer array
- 12: transmission and reception circuit
- 13: pulser
- 14: amplification unit
- 15: AD conversion unit
- 16: beam former
- 17: motion sensor
- 20, 20A, 20B, 20C: apparatus main body
- 21: image generation unit
- 22: display controller
- 23: monitor
- 24: image memory
- 25: lesion detection unit
- 26: pseudo orthogonal cross section generation unit
- 27, 27A: pseudo orthogonal cross section deformation unit
- 29, 29A, 29B, 29C: main body controller
- 30: input device
- 31, 31A, 31B, 31C: processor
- 32: displacement amount estimation unit
- 33: image deformation unit
- 34: measurement unit
- 35: malignancy grade calculation unit
- 41: signal processing unit
- 42: DSC
- 43: image processing unit
- L1: cross section extraction line
- M1: lesion part
- U1: frame image
- U2: pseudo orthogonal cross-sectional image
- U3: normalized pseudo orthogonal cross-sectional image

What is claimed is:

1. An ultrasound diagnostic apparatus that generates a cross-sectional image orthogonal to an observation plane based on a video which is acquired during scanning by an ultrasound probe and in which a lesion part is imaged, the ultrasound diagnostic apparatus comprising:
    a processor configured to
    set a cross section extraction line passing through the lesion part on one frame image among a plurality of frame images constituting the video,
    generate a pseudo orthogonal cross-sectional image orthogonal to the observation plane by arranging, in time series, pixel values on the cross section extraction line in the plurality of frame images, and
    generate a normalized pseudo orthogonal cross-sectional image by non-rigidly deforming the pseudo orthogonal cross-sectional image in a horizontal direction,
    wherein the processor is further configured to
    estimate a displacement amount between a position of a pixel in the pseudo orthogonal cross-sectional image in a case where a scanning speed of the ultrasound probe is made constant and a position of a pixel in the actual pseudo orthogonal cross-sectional image, in each of time points at which the plurality of frame images are captured, and
    non-rigidly deform the pseudo orthogonal cross-sectional image based on the displacement amount.

2. The ultrasound diagnostic apparatus according to claim 1,
    wherein the processor is further configured to
    detect the lesion part from the normalized pseudo orthogonal cross-sectional image, and
    measure a size of the lesion part.

3. The ultrasound diagnostic apparatus according to claim 2,
    wherein the processor is further configured to
    set a plurality of the cross section extraction lines extending in parallel to each other,
    generate a plurality of the pseudo orthogonal cross-sectional images,
    generate a plurality of the normalized pseudo orthogonal cross-sectional images based on the plurality of pseudo orthogonal cross-sectional images, and
    calculate a volume of the lesion part based on an area of the lesion part measured from each of the plurality of normalized pseudo orthogonal cross-sectional images.

4. The ultrasound diagnostic apparatus according to claim 1,
    the processor is further configured to calculate a malignancy grade of the lesion part based on an image in which the lesion part is imaged.

5. The ultrasound diagnostic apparatus according to claim 2,
    the processor is further configured to calculate a malignancy grade of the lesion part based on an image in which the lesion part is imaged.

6. The ultrasound diagnostic apparatus according to claim 3,
    the processor is further configured to calculate a malignancy grade of the lesion part based on an image in which the lesion part is imaged.

7. The ultrasound diagnostic apparatus according to claim 4,
    wherein the processor is further configured to calculate a total malignancy grade obtained by integrating a first malignancy grade calculated based on one of the plurality of frame images and a second malignancy grade calculated based on the normalized pseudo orthogonal cross-sectional image.

8. The ultrasound diagnostic apparatus according to claim 1,
    wherein the processor is further configured to
    detect the lesion part for each of the plurality of frame images, and
    set the cross section extraction line on the frame image with the largest lesion part, among the plurality of frame images.

9. The ultrasound diagnostic apparatus according to claim 2,
    wherein the processor is further configured to
    detect the lesion part for each of the plurality of frame images, and
    set the cross section extraction line on the frame image with the largest lesion part, among the plurality of frame images.

10. The ultrasound diagnostic apparatus according to claim 3,
    wherein the processor is further configured to
    detect the lesion part for each of the plurality of frame images, and set the cross section extraction line on the frame image with the largest lesion part, among the plurality of frame images.

11. The ultrasound diagnostic apparatus according to claim 4,
wherein the processor is further configured to
detect the lesion part for each of the plurality of frame images, and
set the cross section extraction line on the frame image with the largest lesion part, among the plurality of frame images.

12. The ultrasound diagnostic apparatus according to claim 7,
wherein the processor is further configured to
detect the lesion part for each of the plurality of frame images, and
set the cross section extraction line on the frame image with the largest lesion part, among the plurality of frame images.

13. The ultrasound diagnostic apparatus according to claim 8,
wherein the processor is further configured to
detect the lesion part for each of the plurality of frame images, and
set the cross section extraction line on the frame image with the largest lesion part, among the plurality of frame images.

14. The ultrasound diagnostic apparatus according to claim 1,
wherein the ultrasound probe has a motion sensing device configured to detect that detects a moving speed of the ultrasound probe, and
the processor is further configured to estimate the displacement amount based on the moving speed detected by the motion sensor.

15. A control method of an ultrasound diagnostic apparatus that generates a cross-sectional image orthogonal to an observation plane based on a video which is acquired during scanning by an ultrasound probe and in which a lesion part is imaged, the control method comprising:
setting a cross section extraction line passing through the lesion part on one frame image among a plurality of frame images constituting the video;
generating a pseudo orthogonal cross-sectional image orthogonal to the observation plane by arranging, in time series, pixel values on the cross section extraction line in the plurality of frame images; and
non-rigidly deforming the pseudo orthogonal cross-sectional image in a horizontal direction to generate a normalized pseudo orthogonal cross-sectional image,
wherein the control method further comprises:
estimating a displacement amount between a position of a pixel in the pseudo orthogonal cross-sectional image in a case where a scanning speed of the ultrasound probe is made constant and a position of a pixel in the actual pseudo orthogonal cross-sectional image, in each of time points at which the plurality of frame images are captured, and
non-rigidly deforming the pseudo orthogonal cross-sectional image based on the displacement amount.

* * * * *